(12) United States Patent
Flentie et al.

(10) Patent No.: US 11,866,763 B2
(45) Date of Patent: Jan. 9, 2024

(54) SYSTEM, METHOD AND INTERFACE FOR PARALLEL PROCESSING OF ANTIMICROBIAL SUSCEPTIBILITY TESTS USING DIFFERENT SAMPLES

(71) Applicant: SELUX DIAGNOSTICS, INC., Charlestown, MA (US)

(72) Inventors: Kelly Flentie, Charlestown, MA (US); Eric Stern, Charlestown, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 932 days.

(21) Appl. No.: 16/684,056

(22) Filed: Nov. 14, 2019

(65) Prior Publication Data
US 2020/0157597 A1    May 21, 2020

Related U.S. Application Data

(60) Provisional application No. 62/768,206, filed on Nov. 16, 2018.

(51) Int. Cl.
*C12Q 1/20* (2006.01)
*G16H 20/10* (2018.01)
(Continued)

(52) U.S. Cl.
CPC .............. *C12Q 1/20* (2013.01); *C12Q 3/00* (2013.01); *G16H 10/40* (2018.01); *G16H 20/10* (2018.01)

(58) Field of Classification Search
CPC .......... C12M 1/36; C12M 1/34; C12M 41/48; C12Q 1/20; G01N 1/28; G01N 35/028; G01N 35/00732
See application file for complete search history.

(56) References Cited

U.S. PATENT DOCUMENTS 8,349,583 B2 * 1/2013 Green .................... C12Q 1/485
435/31
9,834,808 B2 * 12/2017 Stern ....................... C12Q 1/025
(Continued)

FOREIGN PATENT DOCUMENTS

EP          1160564 A2    12/2001
WO     2011017094 A2     2/2011
(Continued)

OTHER PUBLICATIONS

Microplate on Wikipedia.com (Year: 2018).*
(Continued)

*Primary Examiner* — Hoi C Lau
(74) *Attorney, Agent, or Firm* — Goodwin Procter LLP (57) ABSTRACT

An improved system, method and interface for automated rapid antimicrobial susceptibility testing (AST) is disclosed which includes, in one aspect, a carrier population station comprising a workstation having a graphic user interface (GUI). The GUI accepts information from a lab technologist, including information related to a scope of testing to be performed on a patient sample. The GUI controls intelligent assignment of patient samples to test panels in a manner that maximize utilization of the test carrier by grouping together samples of similar tests scopes and advantageously testing those samples using one multiplexed test panel. Customizing workflow in accordance with test scope to facilitate parallel processing of multiple samples advantageously reduces laboratory waste, decreases test latencies, increases AST system throughput and efficiency, and thus lowers the costs to the AST lab.

11 Claims, 9 Drawing Sheets

(51) Int. Cl.
*G16H 10/40* (2018.01)
*C12Q 3/00* (2006.01)

(56) References Cited

U.S. PATENT DOCUMENTS

| | | | | |
|---|---|---|---|---|
| 9,963,732 | B2* | 5/2018 | Martini | C12Q 1/10 |
| 10,185,923 | B2* | 1/2019 | Fewins | G16H 15/00 |
| 10,619,182 | B2* | 4/2020 | Tada | C12Q 1/008 |
| 10,655,188 | B2* | 5/2020 | Jarvius | C12Q 1/04 |
| 10,829,796 | B2* | 11/2020 | Bork | C12Q 1/14 |
| 11,079,719 | B2* | 8/2021 | Gusyatin | G03H 1/0443 |
| 11,268,126 | B2* | 3/2022 | Stern | G01N 35/00732 |
| 11,268,960 | B2* | 3/2022 | Stern | C12Q 1/04 |
| 11,287,436 | B2* | 3/2022 | Vacic | G01N 35/1095 |
| 11,339,418 | B2* | 5/2022 | Stern | G16B 40/10 |
| 2003/0205511 | A1* | 11/2003 | Olivier | B01L 9/523 422/534 |
| 2007/0020152 | A1* | 1/2007 | Costello, III | B01L 9/523 422/400 |
| 2014/0094971 | A1* | 4/2014 | Thieme | G01N 35/00722 700/275 |
| 2018/0088141 | A1 | 3/2018 | Vacic et al. | |
| 2018/0217172 | A1 | 8/2018 | Webster et al. | |
| 2019/0218591 | A1* | 7/2019 | Vacic | C12Q 1/18 |
| 2019/0323057 | A1* | 10/2019 | Stern | B01L 3/5085 |
| 2020/0024633 | A1* | 1/2020 | Stern | C12Q 1/08 |
| 2020/0157597 | A1* | 5/2020 | Flentie | G16H 20/10 |
| 2022/0145352 | A1* | 5/2022 | Stern | G01N 35/00732 |

FOREIGN PATENT DOCUMENTS

| | | | |
|---|---|---|---|
| WO | 2017218202 A1 | 12/2017 | |
| WO | WO-2017218202 A1 * | 12/2017 | C12Q 1/18 |
| WO | 2018119439 A1 | 6/2018 | |
| WO | 2019071096 A1 | 4/2019 | |
| WO | 2019191328 A1 | 10/2019 | |

OTHER PUBLICATIONS

Invitation to Pay Additional Fees and, Where Applicable, Protest Fee (PCT Article 17(3)(a) and Rules 40.1 and 40.2 (e)), for International application No. PCT/US2019/061473, dated Jan. 27, 2020, 3 pages.
International Search Report and Written Opinion for International application No. PCT/US2019/061473, dated Apr. 2, 2020, 12 pages.
Author unknown, "Microplate", Wikipedia [online] 2018, January [retrieve on Jan. 22, 2020]. Retrieved from Internet URL: https://en.wikipedia.org/w/index.php?title=Microplate&oldid=822943893, 1 page.
Coyle, M.B., ed., "Manual of Antimicrobial Susceptibility Testing", American Society for Microbiology (2005).
Extended European Search Report for EP Patent Application No. 19884872.3, dated Jul. 26, 2022.

* cited by examiner

SYSTEM, METHOD AND INTERFACE FOR PARALLEL PROCESSING OF ANTIMICROBIAL SUSCEPTIBILITY TESTS USING DIFFERENT SAMPLES

RELATED APPLICATIONS

This application is a non-provisional application of, and claims the benefit of priority to U.S. Provisional Application Ser. No. 62/768,206, filed Nov. 16, 2018, entitled "SYSTEM, METHOD AND INTERFACE FOR PARALLEL PROCESSING OF ANTIMICROBIAL SUSCEPTIBILITY TESTS USING DIFFERENT SAMPLES" the entirety of which application is expressly incorporated by reference herein.

BACKGROUND

The present disclosure is related to in vitro diagnostic devices, systems, and methods, particularly microbiological diagnostic devices. The present disclosure relates more particularly to AST testing methods which enhance system throughput and efficiency while reducing test costs by maximizing test carrier utilization.

Antimicrobial susceptibility test (AST) systems evaluate the effectiveness of antimicrobial drugs against sample microbes retrieved from a patient to determine how to best treat the patient. The AST system determines the concentration at which the bacteria stop growing, i.e., the 'minimum inhibitory concentration' (MIC). This may be converted to Qualitative Susceptibility Result (QSR) information, such as the effect of the antimicrobial on the microbe. The MIC or QSR information may then be forwarded to a physician or pharmacist for patient treatment.

AST methods are frequently performed in a central laboratory using a test system that accepts test panel having wells, or 'reaction vessels', that have been pre-populated with different types and/or concentrations of antimicrobials. For example, when testing the effects of an antibiotic such as ampicillin on a patient specimen, each of a plurality of different wells of a panel may be populated with between six and eight concentrations of ampicillin. A patient specimen is also deposited in each well and the effect of the respective antibiotic concentration on the patient specimen is monitored.

Current automated broth dilution AST methods use individual panels with less than 130 reservoirs that have been pre-filled with antimicrobial compounds supplied at the desired testing concentrations. For example, antimicrobials may be selected in accordance with the American Society for Microbiology's "Manual of Antimicrobial Susceptibility Testing" © 2005, for use with a broth micro dilution technique. Furthermore, since available systems commonly test similar numbers of antimicrobials per sample, ie. 10-15 antimicrobials, ordering an "AST" test means receiving information for this number of antimicrobials.

The architecture of an AST panel is correlated to the architecture of the AST system in which it is used, with reservoirs arranged in number and geometry in accordance with the AST inoculation/assay processing system. Although panels having fewer than 130 reservoirs can be processed by less complex AST systems, often it is desirable to test more than 130 different microbials to perform a broad-spectrum analysis to identify targeted treatment for high risk patients. When performing broad-spectrum analysis, multiple 130 reservoir panels are sequentially processed by the AST system and the results are collected and analyzed. Such sequential processing delays treatment in high risk situations.

It would seem desirable to increase the number of reservoirs of a test panel to reduce the need for serial processing, but simply increasing the size of the test panel introduces new challenges. Not only does a larger test panel increase the panel manufacturing costs and AST complexity, it also increases the cost per test for the lab. Furthermore, fundamental limitations to the technologies of current platforms prevent increases in the number of reservoirs without parallel decreases to throughput or sensitivity.

Because state-of-the-art platforms typically can only run 10-15 antimicrobials per test, getting this number of results from an "AST test order" is the clinical standard. This limitation effectively lumps all ASTs together, when in fact the test results can have very different implications for different patients. AST results may be critical for escalating a septic patient to a more powerful antimicrobial from an ineffective empiric antimicrobial and thus save the patient's life. They may also be used to de-escalate from an overly broad empiric therapy delivered intravenously to a more targeted orally available antimicrobial, which may benefit the patient by limiting side effects and also benefit society by decreasing the use of broad-spectrum drugs. At the other extreme, for an otherwise healthy young adult patient who sees an outpatient clinic out of concern for a urinary tract infection, an AST result may be useful strictly for determining a suitable orally available therapy.

Since these patient types currently receive the same AST processing and hospital consolidation has led to laboratory consolidation, consolidated clinical microbiology laboratories must run both sample types, in general with outpatient samples dominating. This design wastes resources and, in the case of septic patients, often provides incomplete information per each test. When broad spectrum analysis is performed on out-patient specimens, a large portion of the AST panel is either unused or the results are ignored. The underutilization of the panel is undesirable for at least the reason that it wastes antimicrobial compounds and uses the same processing overhead to produce fewer results, undesirably increasing the cost of each test to the lab.

SUMMARY

According to one aspect, a method for populating a carrier that supports a plurality of antimicrobial test panels and a plurality of samples to be tested by an Antimicrobial Susceptibility Test (AST) system includes the steps of receiving a test scope, selecting, in response to the test scope, a workflow from among a plurality of different workflows for operating the AST system, each workflow comprising a carrier map associated with the workflow and a prompt, displaying the carrier map associated with the workflow to a user, the carrier map identifying a number of test panels included in the carrier for the workflow, populating the carrier with a test panel based on the carrier map using the prompt, assigning at least one sample to the test panel, storing association information mapping the at least one sample to the test panel, repeating the steps of populating, assigning and storing association information for the number of test panels included in the carrier for the workflow and forwarding the carrier to the AST system, including forwarding the association information for each test panel of the carrier to the AST system.

According to another aspect, a method for performing antimicrobial susceptibility test (AST) methods in an AST system includes the steps of receiving a test scope, executing a workflow associated with the test scope including controlling selection of a test carrier and one or more antimicrobial test panels in response to the test scope, displaying workflow instructions for the selected workflow to control population of the test carrier with a test panel and assignment of at least two different samples to the test panel and performing antimicrobial susceptibility testing on the at least two different samples in parallel with the test panel.

According to a further aspect, a carrier population station of an antimicrobial susceptibility test (AST) system for controlling the population of a carrier with a plurality of test panels and a plurality of test samples for AST processing is disclosed. The carrier population station comprises a processor, a storage device storing workflow program code, operable when executed upon by the processor to control the AST system and a display, coupled to the processor and storage device and configured to provide one or more workflow prompts to a user. The workflow program code is operable when executed upon by the processor to: control a user interface to obtain information related to a test, the information including a test scope and a test carrier identifier; identify, in response to the test scope, a carrier map and a prompt set; display the prompt set to populate the test carrier with a plurality of test panels and a plurality of test samples; and collect test panel and test sample mapping information for the carrier.

According to another aspect, a carrier population station of an antimicrobial susceptibility test (AST) system is provided for controlling the population of a carrier with a plurality of test panels and a plurality of test samples for AST processing. The carrier population station includes a processor, a storage device storing user interface instructions for controlling the AST system and a display, coupled to the processor and storage device, for displaying a user interface controlled by the user interface instructions during operation of the carrier population station, the user interface including input mechanisms for receiving information related to test scopes, test carriers, test panels, and test samples. The carrier population station further includes a workflow, stored in the storage device and associated with a test scope, the workflow operable when executed to display a carrier map and a prompt set to a user, the prompt set controlling selection of a multiplexed test panel and assignment of at least two test samples to the multiplexed test panel.

According to a further aspect, a method for optimizing throughput of an antimicrobial susceptibility test (AST) system which uses test panels having N antimicrobial test wells includes the steps of receiving a test scope identifying a test to be performed on a sample responsive to the received test scope being a test associated with M antimicrobials, M<N, controlling selection of a multiplexed test panel comprising N/M copies of M antimicrobial tests, controlling association of each copy of the antimicrobial tests with a different sample and processing the multiplexed test panel to test the different samples in parallel and thereby optimize AST system throughput.

According to one aspect, a method for optimizing throughput of an antimicrobial susceptibility test (AST) system which uses test panels having N antimicrobial test wells includes the steps of receiving a test scope identifying a test to be performed on a sample, responsive to the received test scope being a test associated with M antimicrobials, M<N, controlling selection of a multiplexed test panel comprising N/M copies of M antimicrobials, controlling association of one copy of N/M copies with the sample, retrieving a second sample of the same test scope and controlling the association of the second sample with a different copy of the N/M copies of M antimicrobials, repeating the steps of retrieving of the samples and associating the samples with the copies of the M antimicrobials until each copy is associated with a sample, and processing the multiplexed test panel to test the different samples in parallel and thereby optimize AST system throughput.

According to a further aspect, a high throughput antimicrobial susceptibility test (AST) system that uses test panels comprising N antimicrobial wells includes a processor, an interface, controlled by the processor and adapted to receive a test scope identifying a test to be performed on a sample, a workflow controller responsive to the received test scope being a test associated with M antimicrobial test wells, M<N, for controlling assignment of a different one of a plurality of samples to each copy of N/M copies of antimicrobials provided on a multiplexed test panel, an inoculation unit for inoculating the multiplexed test panel with the plurality of samples to enable parallel processing of the plurality of samples for improved AST system throughput.

BRIEF DESCRIPTION OF THE DRAWINGS

FIG. 7 is a diagram illustrating exemplary antimicrobial/reservoir mapping for a full spectrum antimicrobial panel;

DEFINITIONS

As used herein, unless specifically indicated otherwise, the word "or" is used in the inclusive sense of "and/or" and not the exclusive sense of "either/or."

Any issued U.S. Patents, allowed applications, published foreign applications, and references that are cited herein are hereby incorporated by reference to the same extent as if each was specifically and individually indicated to be incorporated by reference.

In order for the present invention to be more readily understood, certain terms are first defined below. Additional definitions for the following terms and other terms are set forth throughout the specification.

Antimicrobial: As used herein an antimicrobial refers to an agent that kills (microbicidal), attenuates (microbistatic)

or inhibits the function of a microorganism. An antimicrobial can be a chemical compound, a biological product, such as a peptide, protein, an antibody or a nucleic acid, or a small molecule. It may be naturally occurring product or a synthetic product.

Approximately or about: As used herein, the term "approximately" or "about," as applied to one or more values of interest, refers to a value that is similar to a stated reference value. In certain embodiments, the term "approximately" or "about" refers to a range of values that fall within 25%-1% or less, in either direction (greater than or less than) of the stated reference value unless otherwise stated or otherwise evident from the context (except where such number would exceed 100% of a possible value).

Carrier: As used herein, a "carrier" is a device that supports one or more panels.

Improve, increase or reduce: As used herein, the terms "improve," "increase" or "reduce," or grammatical equivalents, indicate values that are relative to a baseline measurement, such as measurements related to machine throughput, performance or efficiency.

Microorganism: As used herein, a microorganism is an organism such as a bacterium, a virus, protozoa, algae, fungi or any microbial agent which can cause a disease in a human or an animal subject. A microorganism may also remain latent for an indefinite period in a subject and may not ever cause a disease.

Minimum inhibitory concentration (MIC): As used herein, the MIC of an antimicrobial refers to the lowest concentration of the antimicrobial at which concentration its antimicrobial activity is detectable.

Panel: As used herein, a "panel" is a device comprising N reservoirs.

A Comprehensive Panel: As used herein, a "comprehensive panel" is a panel comprising N different reservoirs for storing a variety of antimicrobials, each differing by at least one of a type of concentration, for use in testing a patient sample.

Multiplexed Panel: As used herein, a multiplexed panel is a panel comprising a subset of antimicrobials of the comprehensive panel, the subset being replicated M times for simultaneous testing of M patient samples.

Patient: as used herein, the term "patient" or "subject" refers to any organism to which a provided composition may be administered, e.g., for experimental, diagnostic, prophylactic, cosmetic, and/or therapeutic purposes. Typical patients include animals (e.g. mammals such as mice, rats, rabbits, non-human primates, and/or humans). In some embodiments, a patient is a human. A human includes pre- and post-natal forms.

Qualitative Susceptibility Result (QSR): As used herein, the QSR refers to a determination whether an antimicrobial has an effect on a microbe, and whether a microbe is susceptible to the antimicrobial and vice versa. For example, the microbe stops growth in presence of the antimicrobial, is an indication that the antimicrobial has an effect on the microbe.

Reservoir: As used herein the term reservoir is used to represent a housing space for holding a composition, such as a reagent or a sample, for storage, or for preparation of, or for performing an assay. The term may be used interchangeably with "wells" for example, in a cartridge or a multi-well microtiter panel. A reservoir may be a single well structure. The reservoir may also be in any form and shape, including but not limited to round wells, or wells of any shape or size, or elongated channels. A reservoir is meant to hold a fluid or dried/lyophilized powder substance.

Sample: As used herein, the term "sample" refers to a biological sample, a patient sample, or a microorganism-containing sample.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness in many biological and chemical phenomena.

System/Component/Assembly: As used in this application, the terms "system", "component" or "assembly" are intended to refer to a computer-related entity, either hardware, a combination of hardware and software, software, or software in execution, examples of which are described herein. For example, a component can be, but is not limited to being, a process running on a processor, a processor, a hard disk drive, multiple storage drives (of optical and/or magnetic storage medium), an object, an executable, a thread of execution, a program, and/or a computer. Systems and assemblies are comprised of a plurality of coupled components. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

Target microbe: As used herein, a target microbe is a microbe against which the antimicrobial in question is effective as a microbicidal, microbistatic or inhibitory agent to disrupt a certain function of the microbe relating to its infectivity.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder and/or condition.

Treating: As used herein, the term "treat," "treatment," or "treating" refers to any method used to partially or completely alleviate, ameliorate, relieve, inhibit, prevent, delay onset of, reduce severity of an/or reduce incidence of one or more symptoms or features of a particular disease, disorder, and/or condition. Treatment may be administered to a subject who does not exhibit signs of a disease and/or exhibits only early signs of the disease to decrease the risk of developing pathology associated with the disease.

DETAILED DESCRIPTION

An improved system, method and interface for automated rapid antimicrobial susceptibility testing (AST) includes, in one aspect, a carrier population station comprising a workstation having a graphic user interface (GUI). The GUI accepts information from a lab technologist, including information related to a scope of testing to be performed on a patient sample. The GUI controls intelligent assignment of patient samples to test panels in a manner that maximizes utilization of the test carrier by grouping together samples of similar tests scopes and advantageously testing those samples using one multiplexed test panel. Customizing workflow in accordance with test scope to facilitate parallel processing of multiple samples advantageously reduces laboratory waste, decreases test latencies, increases AST system throughput and efficiency, and thus lowers the costs to the AST lab.

These and other features of the invention will now be described with reference to the figures, wherein like reference numerals are used to refer to like elements throughout.

Figure 1:
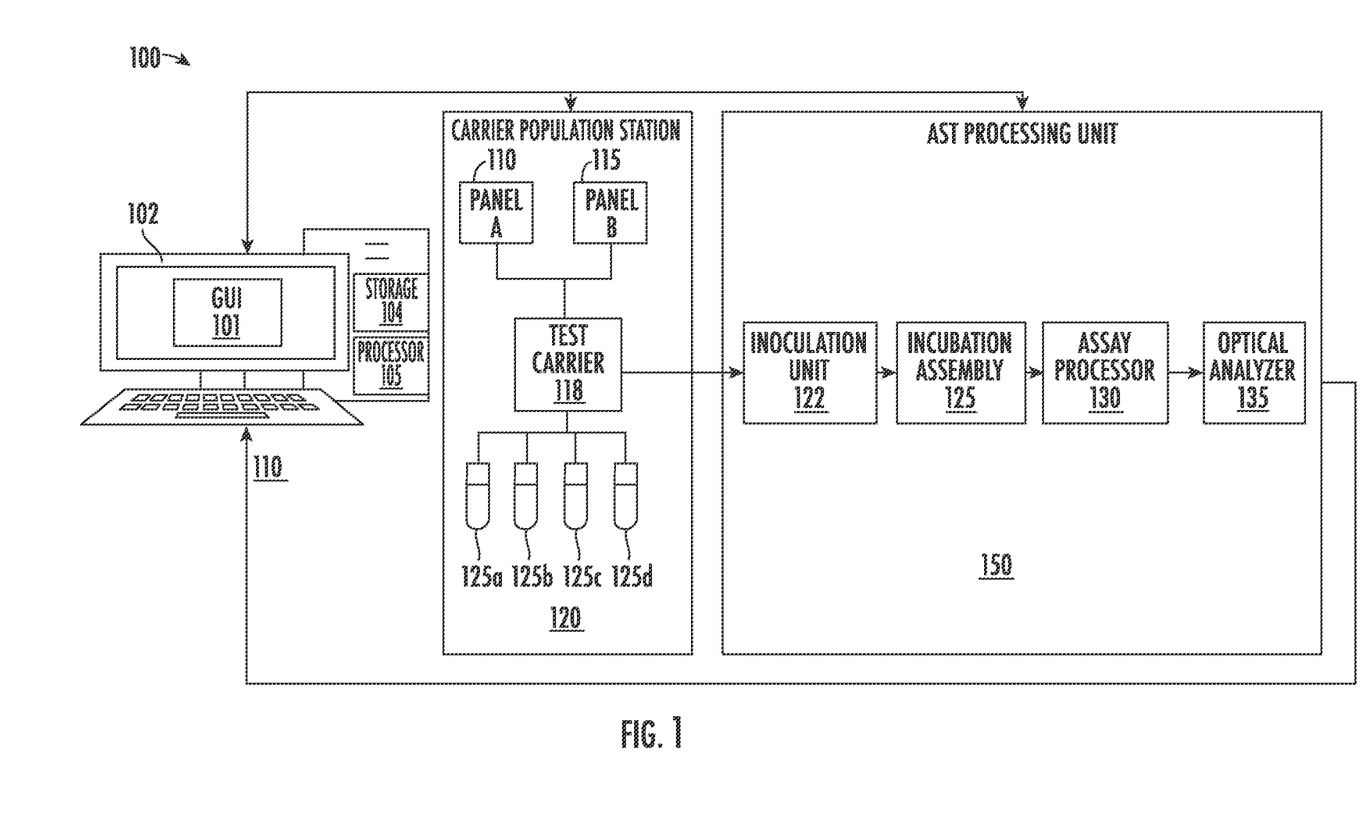
FIG. 1 is block diagram illustrating exemplary components of an antimicrobial susceptibility testing (AST) system incorporating aspects of the invention.

FIG. 1 illustrates exemplary components of one embodiment of an AST system 100 of the present invention which may be provided for use in a clinical testing laboratory or the like. The AST system 100 is shown to include a laboratory workstation 110 coupled to carrier population station 120 and AST processing unit 150. In one aspect, as will be described in more detail below, during operation a laboratory technologist ("lab tech") at the workstation 110 operates in accordance with a workflow to populate a test carrier 118 with antimicrobial panels such as panel A 110 and panel B 115, and patient samples 125a-125d. According to one aspect of the invention, it is realized that a significant cost benefit may be realized by a lab that utilizes workflows which populate multiplexed panels with a plurality of samples to leverage the performance and cost benefits of parallel processing.

The populated test carrier 118 is forwarded to the AST processing unit 150, which includes inoculation unit 122, incubation assembly 125, assay processor 130 and optical analyzer 135. In one embodiment, inoculation, incubation and assay processing is performed using techniques described in U.S. Pat. No. 9,834,808, entitled "Methods for rapid antibiotic susceptibility testing" issued Dec. 5, 2017 to Stern et al. (the '808 patent). However, it is appreciated that other AST platforms exist which would similarly benefit from the methods disclosed herein, including but not limited to the bioMerieux Vitek2®, the Danaher MicroScan®, the Becton-Dickinson Phoenix®, the ThermoFisher Sensi-Titre®, and the Accelerate Diagnostics Pheno®, any of which can be altered according to their particular system architectures and the concepts presented herein by those of skill in the art to realize the utilization and throughput efficiencies of the present invention.

Herein a "test cycle" shall mean the collection of steps performed sequentially on a sample to populate, inoculate, incubate, assay process and analyze the sample's behavior in the presence of different antimicrobials.

In one embodiment, the workstation 110 is a computing device comprising a display 102, a processor 105 (e.g., a central processing unit (CPU), a graphics processing unit (GPU), or both) communicatively coupled to a machine readable storage device 104 (e.g., read only memory (ROM), flash memory, dynamic random-access memory (DRAM) such as synchronous DRAM (SDRAM) or Rambus DRAM (RDRAM), etc.). In one aspect, the storage device 104 includes instructions stored thereon which are operable when executed upon by the processor 105 to display a graphic user interface (GUI) 101 to a laboratory technologist ("lab tech") to control an AST workflow using methods described herein.

The GUI 101 displays workflow instructions to a lab tech to control population of a test carrier and includes input mechanisms that enable the lab tech to provide information related to populated panels and patient samples. The GUI may also include controls permitting the lab tech to launch an AST test. In one aspect, the GUI displays carrier maps and one or more prompts to guide a lab tech through a test carrier population process in a manner that optimizes AST system throughput. The GUI may also include mechanisms to associate test panels, or portions of test panels, with samples.

It should be noted that although the GUI 101 is described as a display of a workstation, the present invention is not limited to the use of any physical medium providing a display and/or control input. In alternate embodiments, the workstation 110 may be a personal computer (PC), a tablet PC, a Personal Digital Assistant (PDA), a cellular telephone, or any machine capable of displaying controls to a laboratory technologist and receiving control from the technologist to responsively execute a set of instructions (sequential or otherwise) that specify actions to be taken by the AST system 100. Further, while only a single workstation 101 is illustrated, the term "workstation" shall also be taken to include any collection of devices that individually or jointly execute a set (or multiple sets) of instructions to perform any one or more of the methodologies discussed herein.

A communications network may connect the workstation 101 to the carrier population station 120 and/or the AST processing unit 150. The network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

At the carrier population station 120, a lab tech, operating in response to and coordination with workflow prompts displayed on GUI 101, selectively populates a test carrier 118 with one or more test panels, such as panel A 110 or panel B 115. One or more samples 125a, 125b, 125c and 125d are associated with each panel of the test carrier. For example, referring briefly to FIG. 6, an example of a test carrier 600 is shown to include 4 panel receptors, such as panel receptor 610, each of which includes one or more protuberances or other coupling elements for securely positioning one or more test panels, such as test panels 602, 604 and 606, on the test carrier 600. The test carrier 600 is shown to include four tube holes 615a, 615b, 615c and 615d, each for accepting a test tube that stores the sample to be tested using the panel.

Figure 6:
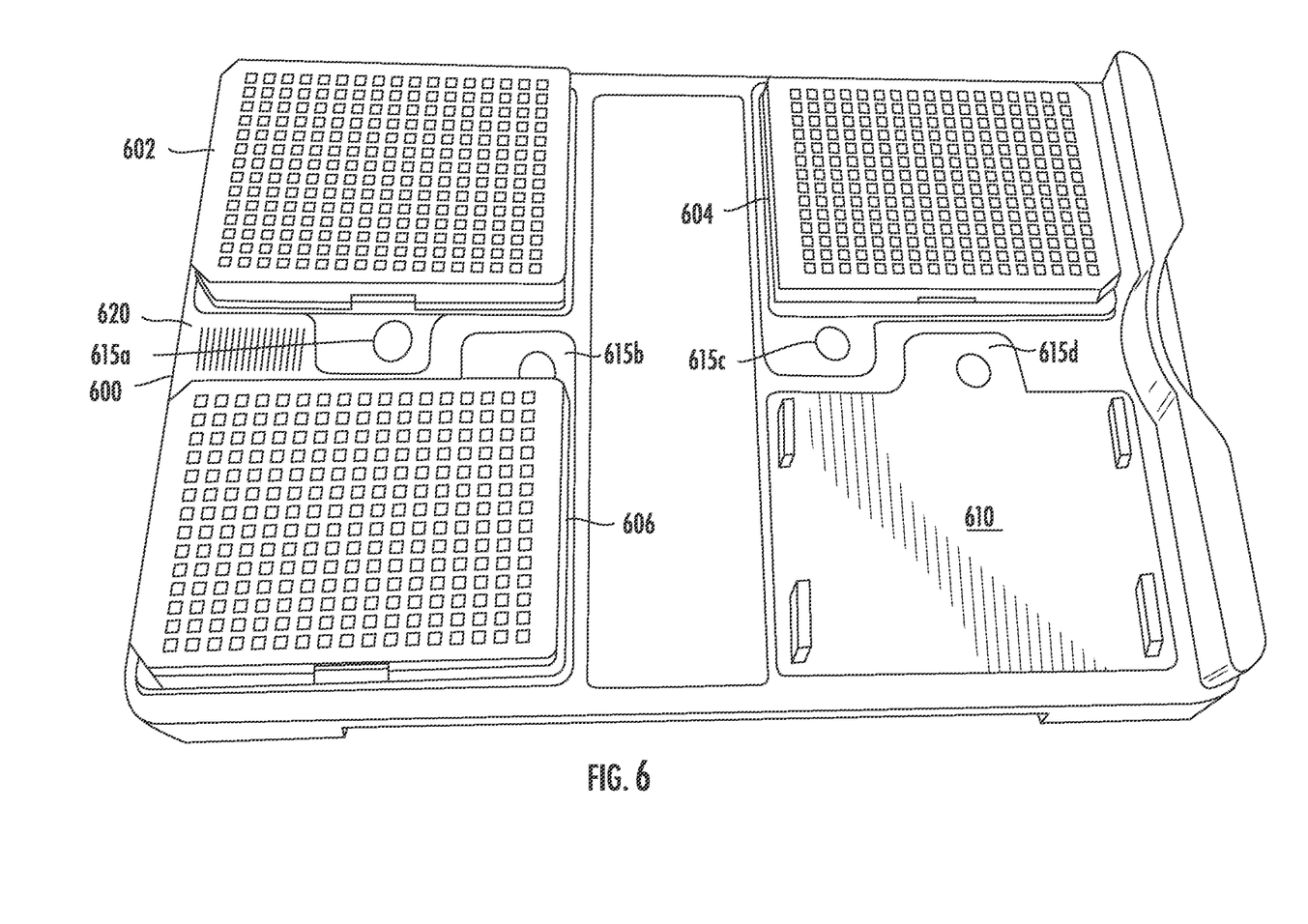
FIG. 6 is a photograph of a carrier and panel arrangement to support full spectrum antimicrobial testing.

In the test carrier of FIG. 6, each test panel is used to test one sample, for example sample provided in tube hole 615a is tested using the antimicrobials provided by panel 602. In this example, the panel 602 is a comprehensive panel that includes a variety of antimicrobials that differ by at least one of a type or a concentration. A map of an exemplary comprehensive test panel having antimicrobials that differ in type or concentration is shown in FIG. 7. In FIG. 7, the intersection of each row and column maps to a reservoir of a test plate, such as reservoir 702. Although antimicrobial types and concentrations are shown, the present invention is not limited to test panels with any particular type or concentration.

In one embodiment, panel A 110 and panel B 115 each comprise a similar reservoir architecture but differ in the population of antimicrobials within the reservoirs. Exemplary panel A 110 may be a comprehensive test panel having a single set of antimicrobials disposed therein, and panel B 115 may be a multiplexed test panel having a replicated subset of the antimicrobials disposed therein. Examples of multiplexed test panels that may be used in the present invention are described in detail in U.S. Provisional Patent Application Ser. No. 62/648,819 filed Mar. 27, 2018 (the '819 application) and incorporated herein by reference. The '819 application describes test panels having sufficient replications of antimicrobial drugs and concentrations to support parallel testing of 2, 3, 4, 5, 6, 7, or 8 microorganism samples.

According to one aspect, workflows operate in response to test scope information to selectively control population of a carrier with test panels, including comprehensive test panels and multiplexed test panels. As mentioned above, multiplexed test panels are test panels on which at least a subset of microbials have been replicated M times, permitting parallel testing of at least M different samples using only one panel. In one embodiment, the workflow prompts the user to select samples of the same test scope for co-population on a single multiplexed panel, thereby decreasing overall test latencies, significantly reducing the waste and consequently the cost of performing AST testing, particularly for the out-patient type testing which may comprise at least 60% of the AST workload.

Figure 8:
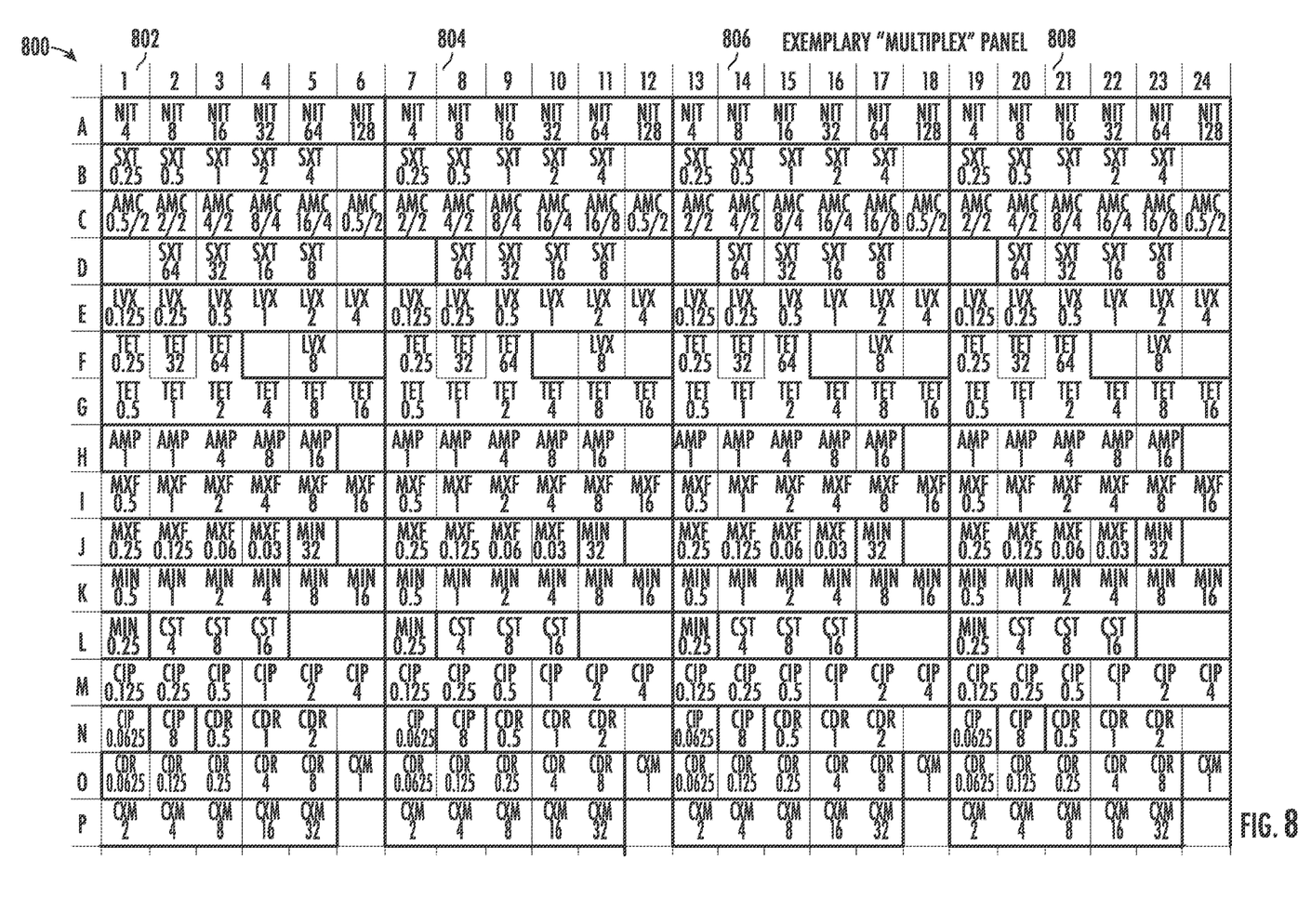
FIG. 8 is a diagram illustrating exemplary antimicrobial/reservoir mapping for a multiplexed antimicrobial panel.

FIG. 8 illustrates an exemplary multiplexed test panel 800, in which a subset of microbials 802 has been replicated four times on panel 800, resulting in antimicrobial copies 802, 804, 806 and 808. The panel 800 may be used, for example, to perform a standard oral antibiotic therapy screening on four different patient samples simultaneously.

Figure 9:
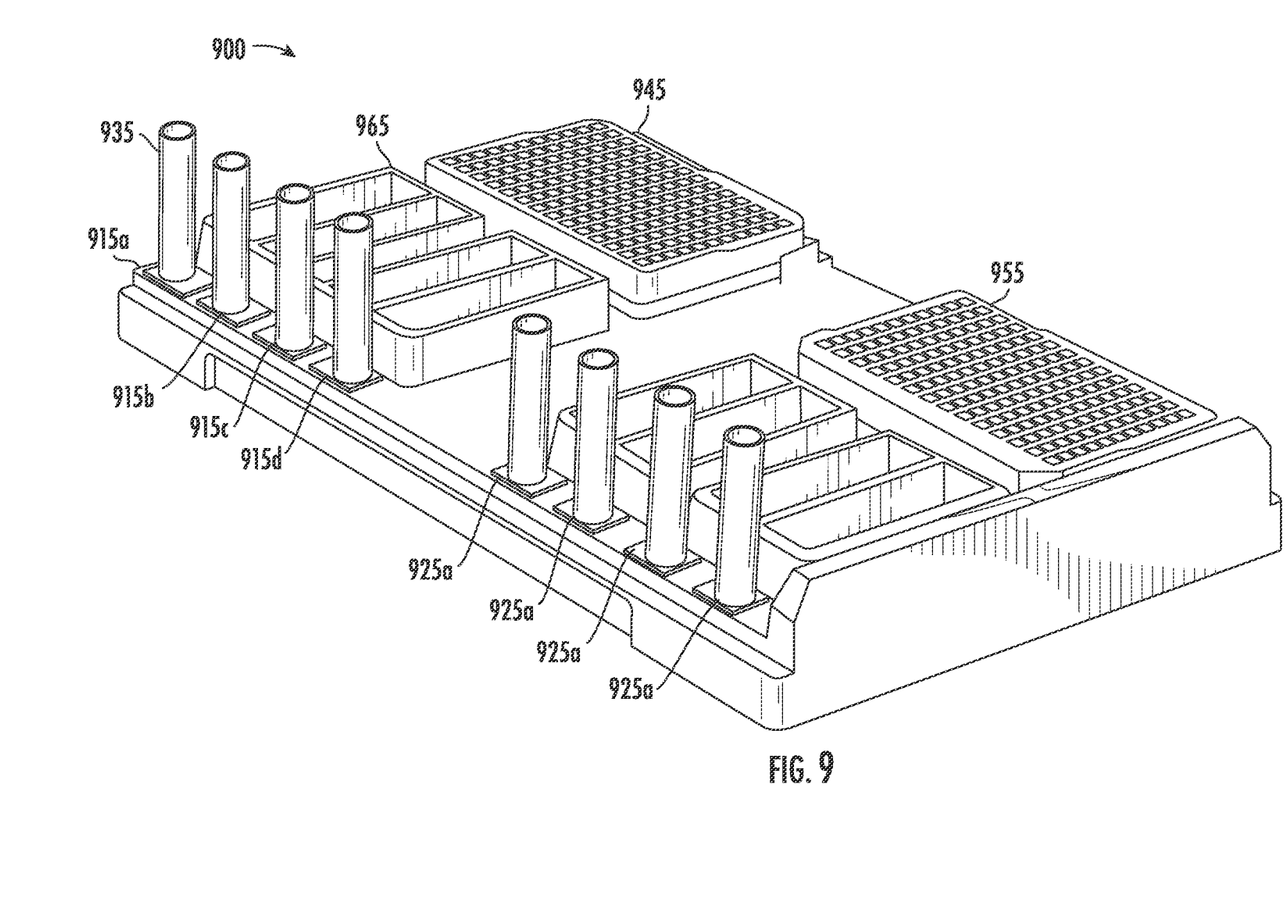
FIG. 9 is an image of a carrier supporting multiplexed panels for parallel processing of multiple samples in a single AST test cycle.

FIG. 9 illustrates one embodiment of a carrier 900 configured to support multiplexed panels 945, 955 which have been populated, for example, with multiple copies of a set of antimicrobials as illustrated in FIG. 8. The carrier includes two panel receptors 946, 947, for engaging panels 945, 955 respectively. The carrier 900 further includes, proximate to each panel, a plurality of test tube holes 915*a*-915*d*, and 925*a*-925*d*, each hole for accepting a test tube such as tube 935 storing a different sample to be tested. Between each test tube 935 and the panel 945 are troughs, such as trough 965. In one embodiment, during inoculation, the samples from the test tubes are transferred to adjacent troughs and combined with a non-selective medium such as Mueller-Hinton broth, tryptic soy agar with lysed equine whole blood, for example as a growth control well. Referring back to FIG. 1, as described above in one embodiment the lab tech populates the test carrier 118 as directed by workflow prompts provided at the GUI 101. Thus, the carrier population station may also include functionality for tracking carriers/samples, such as a barcode reader for use in scanning the carrier or sample test tube barcodes. It should be noted that although a guided process of manual carrier population has been described, it is appreciated that portions of the carrier population workflow may be automated by those of skill in the art, for example using carrier loading hardware and software capable of performing similar functions. Accordingly, the present invention is not limited by the manner of implementation of the carrier population workflow.

Once the test carrier 118 is populated, it may be forwarded to the AST Processing unit 150. As stated above, a patient sample 125*a* is generally received in a barcode labelled test tube. Using a process called broth micro dilution, a patient sample to be assessed is diluted with a broth and introduced to reservoirs containing different antimicrobials at different concentrations by inoculation device 122, such that MICs can be determined for an appropriate panel of antimicrobials. The broth may be cation-adjusted Mueller Hinton broth (MHB) and may contain additional supplements known by those skilled in the art to be advantageous for microbial growth, such as lysed horse blood, and/or for determining antimicrobial efficacies, such as high sodium chloride concentrations. The MHB may be provided by inoculation unit 122 or may be present in dried form on antimicrobial panels 110 and 115.

Once each of the reservoirs are appropriately inoculated, the test carrier 118 is forwarded to incubator 125. Incubator 125 heats the carrier to an appropriate temperature, under appropriate conditions, most preferably aerobic, for growing bacteria. During this time and depending upon the efficacy of the associated antimicrobial for the bacteria, the bacteria may multiply. In some embodiments, as described in PCT Application PCT/2018/54560, filed Oct. 5, 2018, the carrier may be agitated during this growth period, which may be advantageous for dispersing nutrients and/or gas exchange and/or antimicrobials in each well and/or decreasing biofilm formation.

Within zero to eight hours of the AST onset (most preferably zero to four hours), assay testing is initiated by the AST processing unit 130 when a known quantity of signaling agent is added to each well. Adding reagents (including signal generators) may be performed by an automated instrument or a semi-automated instrument or may be performed manually. As described in International Patent Publication No. WO2018/119439 by Stern et al. ("Stern 2018") at ¶¶253 and 372, which is incorporated by reference in its entirety herein, the onset of AST assays may be triggered by the bacteria reaching a pre-determined growth threshold.

Signaling agents (which may be referred to as "sticky-amps") comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary lanthanides include europium and terbium. Exemplary enzymes include horseradish peroxidase, alkaline phosphatase, acetyl cholinesterase, glucose oxidase, beta-D-galactosidase, beta-lactamase, and a combination thereof. The chemical moiety may be conjugated to a signaling agent before contacting the signaling agent to a microorganism, while the signaling agent is initially contacted to a microorganism, or after the signaling agent has contacted a microorganism. Stern 2018 238-246 describes alternative signaling agent chemistries which may be used.

When the signaling agents are added by AST processing unit 130 to AST dilutions containing a microorganism, signaling agent receptors (e.g., moieties that can bind specifically or non-specifically to a microorganism) associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are "free" in solution, as defined by those not bound to intact bacteria. Note that free signaling agents may be bound to soluble microbial components if, for example, microorganisms lyse in response to antimicrobial treatment.

As disclosed in the '808 patent, the number of signaling agents that associate with and/or intercalate into microorganism surfaces is proportional to the microorganism surface area, which is strongly associated with truly resistant microorganisms. The AST processing unit 130 translates microorganism surface area (rather than volume) into a measurable signal, most preferably an optical signal. The optical signals from each carrier reservoir may then be optically analyzed by optical analysis unit 135 to determine the concentration (if any) of bacteria remaining in a test reservoir. Optical analysis unit 135 computes an MIC in accordance with the results and forwards that information to the lab tech for reporting to the treating physician or pharmacy.

As disclosed in Stern 2018 at 197-246, a plurality of assays may be performed before, after, or in parallel with the surface binding assay. Such assays can include, without limitation, metabolic assays, nucleic acid assays, enzymatic assays, etc.

Figure 2:
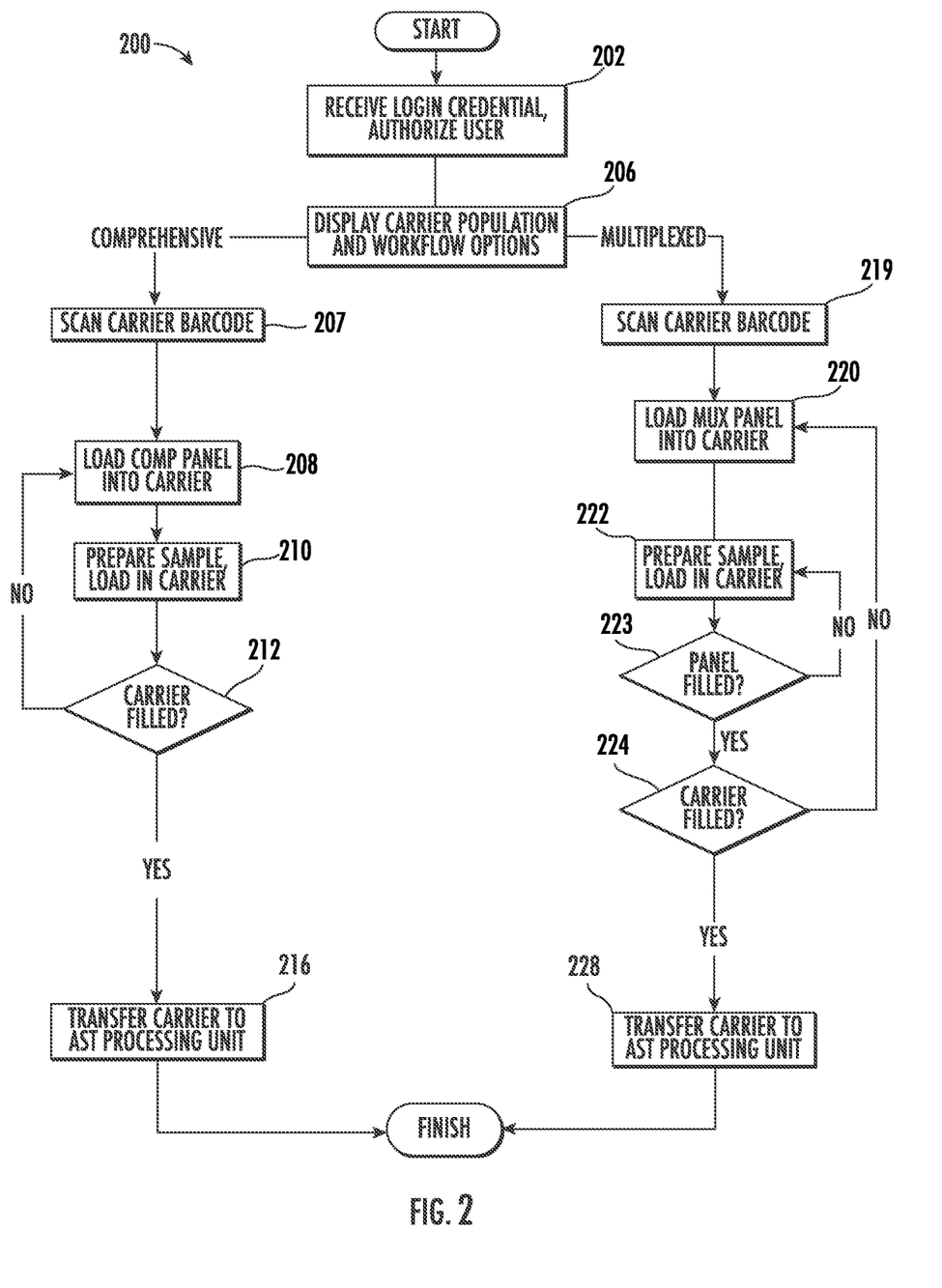
FIG. 2 is a flow diagram of a various workflows that may be implemented in the system of FIG. 1 for carrier population according to aspects of the invention.

FIG. 2 illustrates exemplary steps of a workflow that may be used to control test carrier population at the carrier population station 120. At step 202 the lab tech may be authenticated at the system, although to streamline workflows in some embodiments this step may be performed only periodically. At step 206 the carrier population station 120 displays test scope options to the lab tech using GUI 101.

Figure 3A:
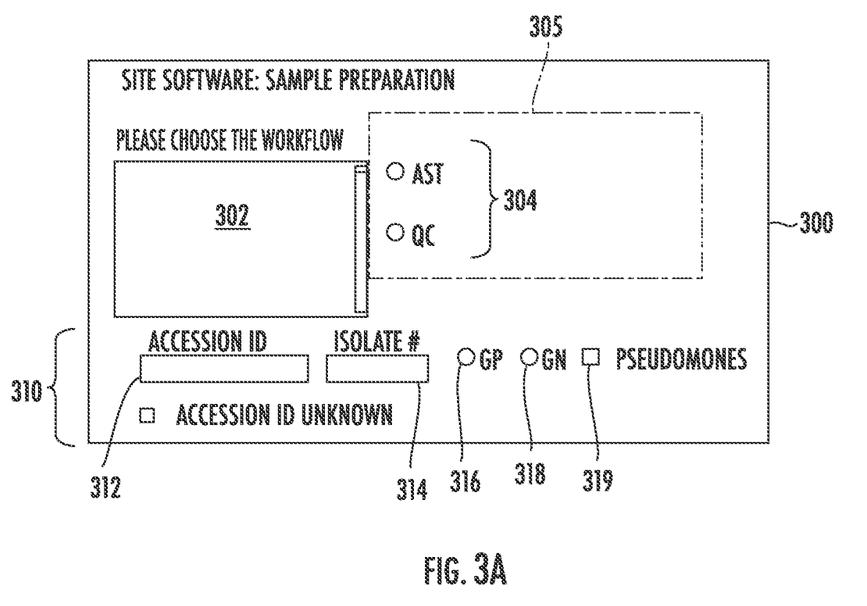
FIGS. 3A and 3B illustrate exemplary embodiments of interface windows of a graphic user interface (GUI) for use in the AST system of FIG. 1.

An example of one workflow window 300 that may be displayed by GUI 101 at step 206 is illustrated in FIG. 3A. In one embodiment, workflow window 300 comprises a portion of a monitor's display screen which is controlled by software operating on workstation 110 and communicating with the carrier population station 120 and the incubation/assay processing unit 150. The window includes mechanisms for collecting input data related to each test cycle and for displaying workflow prompts to intelligently direct population of the carrier in a manner that optimizes utilization of the carrier.

Display window 300 is shown generally apportioned into three areas; a carrier map 302 area, workflow prompt area 305 and sample information area 310. According to one aspect, and as will be described in more detail below, the workflow prompt area 305 may include both input mechanisms, for receiving control information from the lab tech, and text that directs the lab tech during carrier population. Workflow prompt area 305 is shown to include workflow option input mechanisms 304 to define the workflow type for a test cycle. The example of FIG. 3A illustrates two test cycle options, including AST and Quality Control (QC) test cycles.

As will be described in more detail below, depending upon the particular workflow and test scope selected by a lab tech, the carrier map area 302 provides a visual representation of the test carrier and its population progress.

Sample information area 310 includes fields and/or other input mechanisms for uniquely identifying the sample (such as Accession ID 312 and Isolate #314) and for receiving attribute information for the sample (such as GP 316, GN 318 or Pseudomonas 319).

Figure 3B:
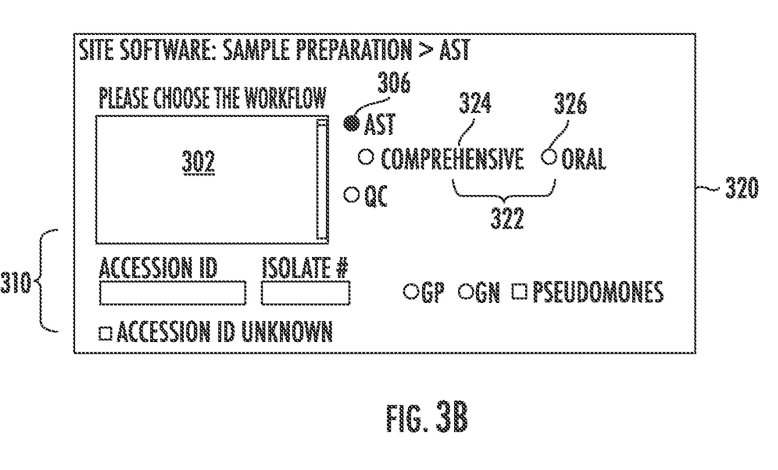

FIG. 3B illustrates a second window 320 that may be displayed by the GUI 101 at step 206 in response to selection of an AST workflow option 306. Selection of an AST workflow option 306 causes GUI 101 to display test scopes 322 to the user, wherein the test scopes are shown to include a comprehensive test 324 type and an oral test 326. A comprehensive test 324 may be differentiated from an oral test 326 by the available microbials of each test, where the oral test 326 evaluates a smaller variety of antimicrobials than the comprehensive test.

Although the choices made available as test scope 322 include 'comprehensive' and 'oral', it can be appreciated that any label may be used to differentiate test scopes. In general, according to one aspect a test scope is differentiated by the number and/or type of antimicrobial provided by a test panel and concomitantly the number of therapies available for treatment. Thus, test scopes may differ based on a patient type (inpatient vs. outpatient), a requestor type (hospital vs. clinic or pharmacy), or a therapy type (oral or intravenous), etc. Tests of relatively limited scope may benefit from the use of a multiplexed panel architecture which enable parallel processing of multiple samples. According to one aspect, workflows are designed to optimize carrier utilization by grouping together samples requiring testing of similar scopes to realize the benefits of a multiplexed panel architecture. Thus, although two test scope options are shown in FIG. 3B, each of which inherently relate to two different panel architectures (comprehensive and multiplexed), it is appreciated that some systems may include a variety of different panel architectures (for example, having different degrees of multiplexing), and in such systems there may be a like variety of test scopes and workflows, each of which drive the population of the carrier to maximize AST throughput.

Referring back to FIG. 2, if at step 206 the lab tech selects a comprehensive panel workflow, then at step 207 an empty carrier is introduced to system and an identification barcode is advantageously scanned, enabling the lab tech to track the carrier through the system. At step 208 a comprehensive panel is loaded into the carrier. At step 210, the sample is prepared, the test tube scanned to associate it with the comprehensive panel, and it is loaded into the carrier. At step 212 it is determined whether the carrier is full, and if not, the process returns to step 208, where the lab tech is prompted to load another comprehensive panel and associated sample until the carrier is determined full at step 212. At that point, the carrier is transferred to the Assay Processing Unit at step 216.

Figure 4A:
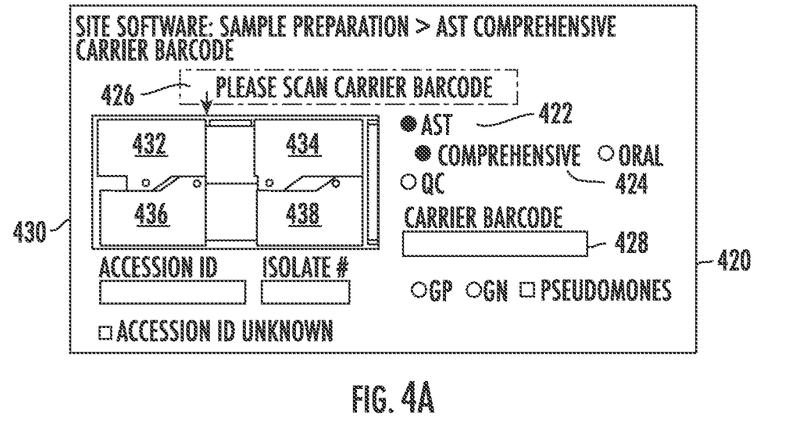
FIGS. 4A, 4B and 4C illustrate exemplary embodiments of interface windows of a GUI that may be used to control the population of AST carriers with multiple antimicrobial panels.
Figure 4B:
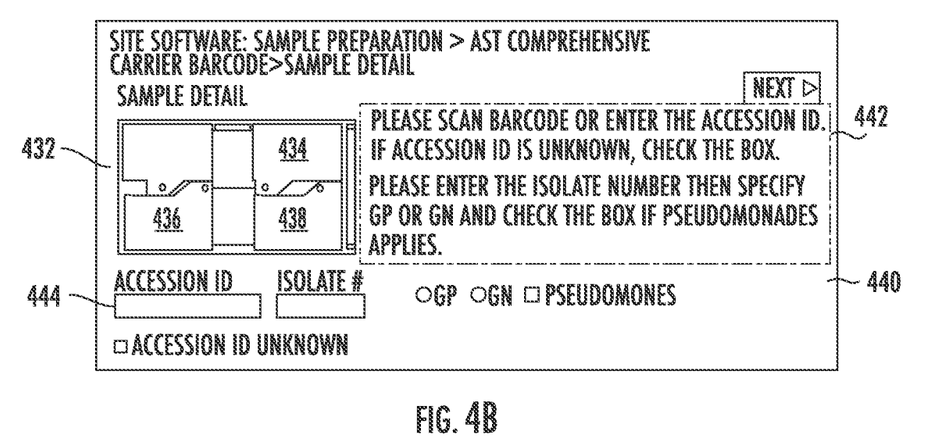
Figure 4C:
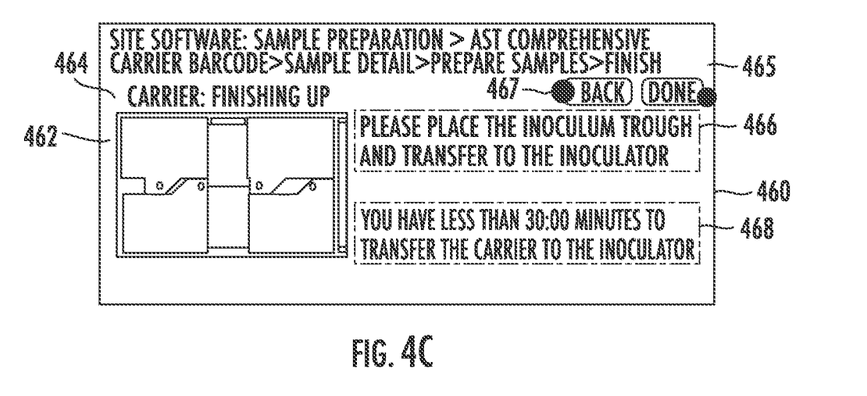

FIGS. 4A-4C illustrate exemplary windows that may be displayed at the GUI to control the population of the carrier using the processes of steps 208-216 of FIG. 2. In window 420 of FIG. 4A, and AST 422/comprehensive 424 test scope is shown selected. In one embodiment, the selection of a comprehensive workflow results in display of carrier map 430 in the carrier map area of the window 420. The carrier map 430 includes visual representations of four comprehensive panels, 432, 434, 436 and 438. In one embodiment, each comprehensive test panel includes 384 reservoirs, and a carrier is capable of supporting four comprehensive panels.

The GUI prompts the lab tech, for example by providing workflow prompt 426 ("Please Scan Carrier Barcode"). Other methods of prompting the lab tech include, for example, highlighting or otherwise visually differentiating the next input field for the workflow (here carrier barcode field 428). Although visual prompts are shown, it is appreciated that audio prompts may also be incorporated or substituted.

In FIG. 4B, following receipt of a carrier barcode (step 207, FIG. 2), a GUI window such as 440 may be displayed to the lab tech. In GUI window 440, panel 432 is shown as a highlighted working panel, and the sample input portion 410 of window 440 is also featured to prompt appropriate input of the sample information. An instruction prompt 442 is also provided to guide the lab tech through the workflow. In the embodiment of FIG. 4B, the carrier population station 120 prompts for entry of information related to the sample that is to be used with panel 432, including an accession number. Accession numbers (used in clinical laboratories) are unique identifiers given to patient samples when they are submitted for testing. The lab tech may also be prompted to enter other sample information, including attributes of the sample such as whether the sample is known to be a certain type of bacteria, such as a Gram Negative (GN) or Gram Positive (GP) organisms, or a *Pseudomonas* spp. bacterium.

FIG. 4C illustrates an exemplary window that may be displayed following receipt of sample information (FIG. 2, step 210). Sample icon 464 is shown populated to visually indicate receipt of sample information. The lab tech will then be prompted whether the carrier is full (FIG. 2, step 211). If not full, the lab tech is given the option to load another panel and sample, repeating steps 208 and 210. The process of loading panels into the carrier continues until it is determined (FIG. 2, step 212) that the carrier is complete or until the user does not wish to load more panels. At this point, the lab tech may select a launch button ("Done" 465) and the carrier may then be transferred to AST processing unit 150. Should the lab tech need to modify any sample or carrier information prior to panel inoculation, the lab tech may navigate back to any other window using the navigation button 467.

Referring back to FIG. 2, the process undertaken when populating a carrier using multiplexed panels will now be described with regard to FIGS. 5A-5C. At step 220, an empty carrier is introduced to system and an identification barcode is advantageously scanned, enabling the lab tech to track the carrier through the system. At step 222 the first sample is prepared and assigned to the panel. In one embodiment, the sample may be included in a barcode identified test vial, and the step of preparing the sample may include assigning the barcode of the vial to the respective panel. At step 223 it is determined whether space remains in the panel for another sample. If space remains on the panel for one or more additional samples, the lab tech is prompted to load another sample and/or advantageously scan its barcode and/or enter sample information. If the panel is full or if the lab tech does not wish to load additional samples, the lab tech may proceed to step 224. At step 224 it is determined whether space remains in the carrier for accepting another panel. If space remains population of the carrier is determined at step 224 not to be complete and the process returns to step 220, where another multiplexed panel is loaded into the carrier and a sample is inoculated in the panel. The process of loading multiplexed panels into the carrier at step 220 and assigning samples to the multiplexed carriers at steps 223, 224 are repeated until it is determined at step 224 that the carrier is full or until the user does not wish to load more panels, at which point the populated carrier may be forwarded to the AST processing unit 150.

Figure 5A:
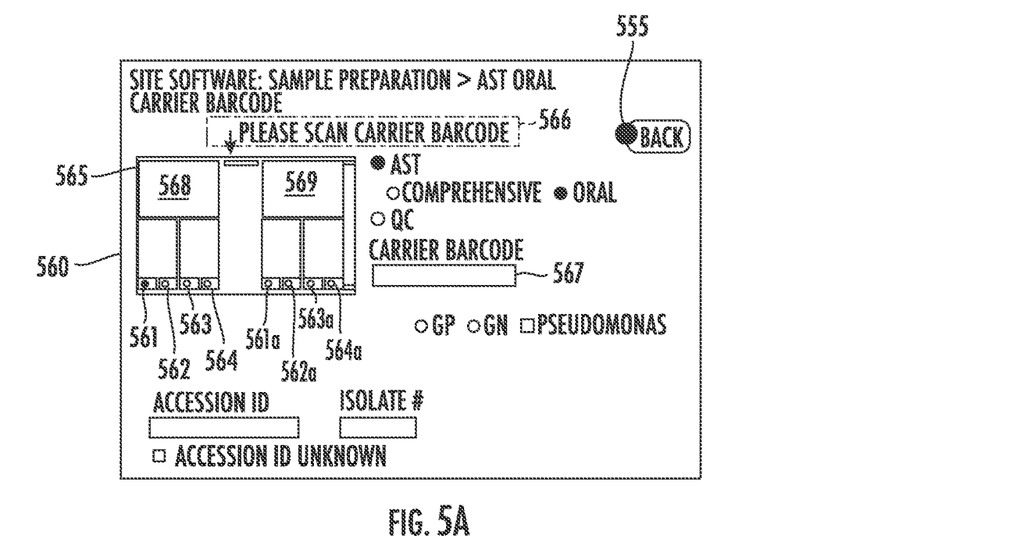
FIGS. 5A, 5B and 5C illustrate exemplary embodiments of interface windows of a GUI that may be used to control the population of AST carriers with multiple antimicrobial panels for multiple patient samples.
Figure 5B:
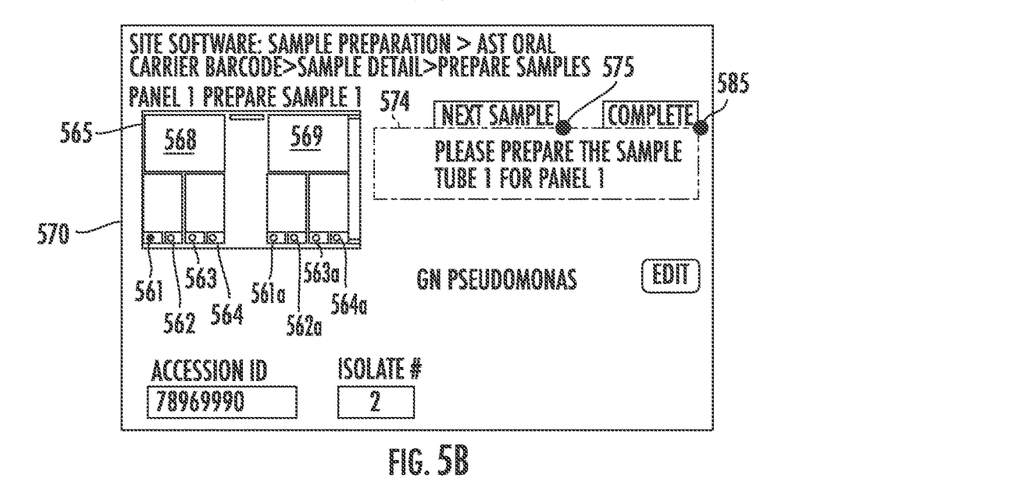
Figure 5C:
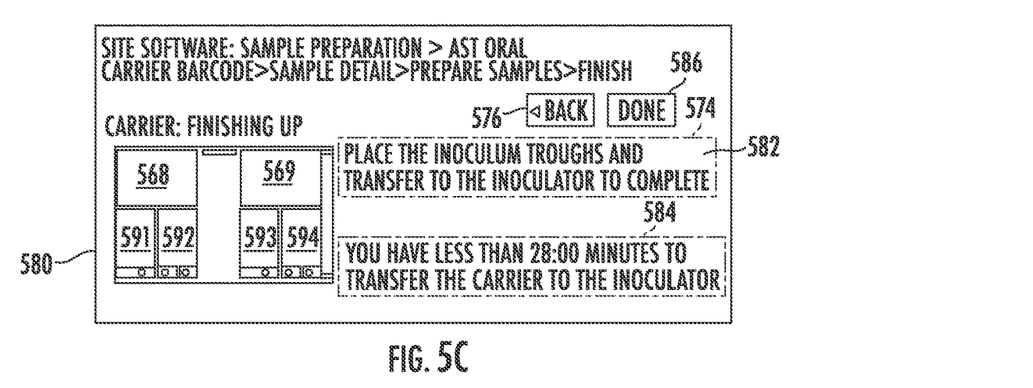

FIGS. 5A-5C illustrate exemplary GUI windows that may be provided to facilitate the workflow described above for reduced size panels. As shown in FIG. 5A, responsive to the test scope being one that would benefit from the use of multiplexed panels, a multiplexed panel carrier map 565 and associated workflow instructions/prompts 566, 567 are displayed to the lab tech. In one aspect, carrier map 565 enables interactive association of different samples with different panels on a single carrier. Panel 568 is preferably a multiplexed panel as described in the '819 patent application; that is, it is a single panel that comprises between 2, 3, 4, 5, 6, 7, 8, 9, 10, 12, 16, 32 or 48 copies of a subset of antimicrobials from the comprehensive panels, although any panels that are adapted for parallel processing of patient samples may be substituted herein. In the example of FIG. 5A, the panel comprises two multiplex antimicrobial panels, 568 and 569, each of which may support parallel testing of up to four independent samples, 561-564 and 561*a*-564*a*.

As with the comprehensive workflow process, the multiplex panel workflow process initiates with a capture of the bar code of the carrier. As such, a prompt 566 is displayed to the lab tech, and the carrier barcode input field 567 is advantageously highlighted. Following capture of the carrier barcode, panel 568 may be shown highlighted as in FIG. 5B to represent to the lab tech that it is the working panel, and the lab tech may select a sample input number 561. When selected, the lab tech may be prompted to input sample information data as described in FIG. 4B. When sample information entry for sample 561 is complete, the lab tech may proceed with making the next sample for the panel, 562, beginning by using navigation button 575. This may be repeated until the panel is fully occupied with samples or until the lab tech has no more samples. After the lab tech has completed work on panel 568, panel 569 may optionally be loaded with samples similarly. When panels and samples are fully loaded, the GUI may alert the user to place dilution troughs 591-594 in the carrier by highlighting which need to be added for the number of samples loaded, 591 and 593 as shown in FIG. 5C.

The lab tech may use the different features of the GUI 101 to selectively populate panels with samples, until the carrier is maximally utilized. The lab tech may then use navigation buttons 576 and 586 to either modify panel/sample mappings or alternatively forward the populated carrier to AST processing unit.

Although the process of FIG. 2 describes two workflows which each populate carriers using one type of panel, it is not a requirement that each carrier include only one type of test panels. In fact, because the number of reservoirs of each type of test panel are the same, regardless of panel type, it is envisioned that the workflows may be adapted by those of skill in the art to populate a carrier with a variety of different types of test panels, to provide a variety of different tests of different scope on the same carrier within a single test cycle. Therefore, the present invention is not limited to carriers that support one test panel type per test cycle.

Accordingly, a system, method and interface for performing AST methods in a manner that increases system utilization, throughput and efficiency while reducing waste and overhead costs has been shown and described. The method provides interfaces and workflows that tailor the population of a carrier according to the scope of testing to be performed on test samples in a manner that groups tests of similar scope to leverage the benefits of parallel processing made possible by multiplexed test panels.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of functional blocks or units that might be implemented as program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but still co-operate or interact with each other.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single embodiment to streamline the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A method for performing antimicrobial susceptibility test (AST) methods in an AST system, the method comprising the steps of:
   providing an AST system comprising at least one test carrier, each test carrier comprising at least one panel receptor configured to securely position an antimicrobial test panel;
   receiving a test scope through a graphical user interface (GUI) of a workstation;
   executing a workflow associated with the test scope including controlling selection of a test carrier and one or more antimicrobial test panels in response to the test scope;
   displaying workflow instructions on the GUI of the workstation for the selected workflow to control population of the test carrier with one or more antimicrobial test panels;
   grouping at least two samples together requiring similar test scopes;
   assigning one or more sample groups to the antimicrobial test panels, wherein the assignment is configured to maximize at least one of utilization of the test carrier, reduction of laboratory waste, decrease in test latencies, or combinations thereof;
   performing antimicrobial susceptibility testing on the at least two different samples in parallel with the one or more antimicrobial test panels; and
   collecting results of the antimicrobial susceptibility testing.

2. The method of claim 1 wherein the antimicrobial test panel is selected from a set of antimicrobial test panels including a first panel populated with a first set of antimicrobials and a second panel populated with a second set of antimicrobials, wherein the second set of antimicrobials comprises at least two replicated subsets of antimicrobials.

3. The method of claim 2 wherein the test scope relates to one of a patient type, a therapy type, a requestor type, an antimicrobial set or a combination thereof.

4. The method of claim 2 wherein each sample of the at least two different samples is associated with a different subset of the at least two replicated subsets of antimicrobials.

5. The method of claim 1, wherein the workstation is selected from the group consisting of a computing device, a personal computer, a tablet personal computer, a personal digital assistant, a cellular telephone, collections of devices thereof, or combinations thereof.

6. The method of claim 1, further comprising the steps of assessing if space remains on the test carrier for an additional panel, and if the carrier is assessed as having space available for an additional panel, displaying a prompt indicating that the space is available.

7. The method of claim 1 wherein the test scope relates to a number of different antimicrobials provided by the antimicrobial test panel.

8. The method of claim 1 wherein the test scope relates to an architecture of the antimicrobial test panel.

9. The method of claim 1 wherein a prompt directs a user to position the antimicrobial test panel at a location within the test carrier.

10. The method of claim 1 wherein at least two antimicrobial test panels are positioned within the test carrier.

11. The method of claim 1 wherein the antimicrobial test panel comprises a multiplexed test panel and at least two samples are assigned to the multiplexed test panel.

* * * * *